(12) United States Patent
Ma

(10) Patent No.: US 7,092,752 B2
(45) Date of Patent: Aug. 15, 2006

(54) SKIN ACUPOINT/MERIDIAN NITRIC OXIDE COLLECTION KIT AND METHOD THEREOF

(75) Inventor: Sheng-Xing Ma, 1124 W. Carson St., Torrance, CA (US) 90502

(73) Assignee: Sheng-Xing Ma, Torrance, CA (US)

( * ) Notice: Subject to any disclaimer, the term of this patent is extended or adjusted under 35 U.S.C. 154(b) by 649 days.

(21) Appl. No.: 10/206,814

(22) Filed: Jul. 27, 2002

(65) Prior Publication Data
US 2004/0024332 A1 Feb. 5, 2004

(51) Int. Cl.
*A61H 39/02* (2006.01)

(52) U.S. Cl. .................. 600/548; 600/562; 604/23

(58) Field of Classification Search ........... 600/562, 600/563, 565, 571, 572, 573, 580; 604/23, 604/312, 313
See application file for complete search history.

(56) References Cited

U.S. PATENT DOCUMENTS

| | | | | |
|---|---|---|---|---|
| 4,224,941 A | * | 9/1980 | Stivala | 604/23 |
| 4,605,399 A | * | 8/1986 | Weston et al. | 604/305 |
| 4,627,842 A | * | 12/1986 | Katz | 604/177 |
| 5,154,697 A | * | 10/1992 | Loori | 604/23 |
| 5,462,052 A | * | 10/1995 | Gehrich et al. | 600/323 |
| 5,607,391 A | * | 3/1997 | Klinger et al. | 604/33 |
| 5,788,682 A | * | 8/1998 | Maget | 604/290 |
| 6,000,403 A | * | 12/1999 | Cantwell | 128/888 |
| 6,019,735 A | * | 2/2000 | Kensey et al. | 600/573 |
| 6,149,606 A | * | 11/2000 | Alving et al. | 600/562 |
| 6,432,077 B1 | * | 8/2002 | Stenzler | 604/23 |
| 6,458,109 B1 | * | 10/2002 | Henley et al. | 604/304 |
| 6,572,594 B1 | * | 6/2003 | Satterfield et al. | 604/290 |
| 6,670,323 B1 | * | 12/2003 | Looker et al. | 514/6 |

* cited by examiner

*Primary Examiner*—Max F. Hindenburg
*Assistant Examiner*—Rene Towa
(74) *Attorney, Agent, or Firm*—Raymond Y. Chan; David and Raymond Patent Group

(57) ABSTRACT

A skin acupoint/meridian nitric oxide collection kit comprises a nitric oxide collecting solution; a collecting system comprising a guiding body having a collecting cavity and a skin window. When the nitric oxide collecting solution is received inside the collecting cavity of the guiding body and the collection kit is applied to the skin surface, the nitric oxide collecting solution is exposed to the skin surface through the skin window; an adhesive element made of adhesive material for attaching and positioning said guiding body on the skin surface such that said guiding body is provided on a predetermined position of the skin surface and the nitric oxide collecting solution is retained inside said collecting cavity on the predetermined position of the skin surface; means for injecting said nitric oxide collecting solution; and means for collecting said nitric oxide collecting solution.

11 Claims, 9 Drawing Sheets

Provide a NO collecting solution having a predetermined concentration on a predetermined position of a skin surface for a predetermined period of time

↓

A final solution is formed

↓

Collect the final solution

FIG. 8

SKIN ACUPOINT/MERIDIAN NITRIC OXIDE COLLECTION KIT AND METHOD THEREOF

BACKGROUND OF THE PRESENT INVENTION

1. Field of Invention

The present invention relates to a skin acupoint/meridian nitric oxide collection kit and method thereof, and more particularly to a skin acupoint/meridian nitric oxide collection kit and method for collecting nitric oxide, nitrite and nitrate for assaying nitric oxide concentration on a skin surface.

2. Description of Related Arts

Nitric oxide (NO) levels are predominantly increased in skin acupoints or meridians, and NO is an important meridian chemical. Collections of NO, nitrite, and nitrate from skin surface will make it possible to assay NO concentrations from the acupoints or meridians for research, diagnosis, and treatment of skin and related disorders using alternative therapies such as acupuncture, acupressure, chiropractic medicine, therapeutic touch, Reiki, Tuna, laying-on-of-hands, and Qi Gong.

Recent studies have shown that NO is perhaps one of the most important messenger molecules in the human body, which is produced in many cell types including neurons and skin tissues. Nitric oxide concentrations and chemical messengers in human skin can be continuously monitored by using dermal microdialysis in vivo. (Clough G F, Bennett A R, Church M K: Measurement of nitric oxide concentration in human skin in vivo using dermal microdialysis. Exp Physiol 1998; 83: 431–434; Clough G, Bennett A R, Church M K: Relationship between nitric oxide, cyclic GMP and vasodilatation in human skin in vivo. J Physiol 1998; 513P). However, the procedure of such method requires a step of inserting a needle into the human's skin, which is painful. Thus, it may have possible side effects and cause infections through the needle.

In a living system, oxyhemoglobin and oxymyoglobin catalyze the complete conversion of NO or nitrite ions ($NO_2^-$) to nitrate ions ($NO_3^-$). Measurements of the metabolites, that is, nitrite or nitrate ions, have been considered to be very adequate indicators of the presence of NO. (Ma S X, Lgnarro L J, Byrns R, Li X Y: Increased nitric oxide production in posterior hypothalamus and central sympathetic function on arterial pressure tolerance to nitroglycerin in rats. Nitric Oxide: Biology and Chemistry 1999: 3: 153–161). However, there is no such a kit for collecting nitrate, nitrite, and NO on skin surface.

The chemicals and mechanism of the acupoints or meridians, including the mechanisms and the substances of meridian transmission in many alternative therapies such as acupuncture, therapeutic touch, and Qi Gong acupuncture, therapeutic touch, and Qi Gong are unexplored. Meridian system has remained a mystery for thousands of years. None of similar products has been used for collecting and determining nitric oxide concentrations in acupuncture points or meridians as well as studying mechanism responsible for nitric oxide in the meridians and their responses to alternative therapies. Recent use and acceptance of alternative therapies such as acupuncture, therapeutic touch, and Qi Gong throughout the world shows us that there is a need to study the mechanisms or systems of meridian systems so that we may master the science of alternative therapies effectively and efficiently.

SUMMARY OF THE PRESENT INVENTION

It is an object of the present invention to provide a skin acupoint or meridian nitric oxide collection kit to collect nitrite, nitrate and nitric oxide from human's skin surface or animal's skin surface for determining nitric oxide (NO) concentrations in acupuncture points or meridians, so as to assay nitric oxide concentration on a skin surface effectively.

It is another object of the present invention to provide a skin acupoint or meridian nitric oxide collection kit, which is an improvement or addendum to the existing products such as nitrogen oxide analyzer (Dasibi, Glendale, Calif.), nitric oxide system (Harvard Apparatus, Inc., USA), nitric oxide measuring system (Inter Medical Co., Ltd., Japan), and Iso-NO (World Precision Instruments, Inc., USA) for widening their usable area to assay nitric oxide, nitrite and nitrate from skin acupoints or meridians.

It is another object of the present invention to provide a skin acupoint or meridian nitric oxide collection kit, wherein the procedure thereof is painless, non-toxic and lack potential infections and side effects.

It is another object of the present invention to provide a skin acupoint or meridian nitric oxide collection kit, wherein collections of nitric oxide (NO), nitrite and nitrate from the skin surface using the collection kit of the present invention will assay NO concentrations from the acupoints or meridians for research, diagnosis, and treatment of skin and related disorders using alternative therapies such as acupuncture, acupressure, chiropractic medicine, therapeutic touch, Reiki, Tuna, laying-on-of-hands, and Qi Gong.

It is another object of the present invention to provide a skin acupoint or meridian nitric oxide collection kit for assaying nitric oxide concentration on a skin surface for studies of alternative therapies.

It is another object of the present invention to provide a skin acupoint or meridian nitric oxide collection method for assaying nitric oxide concentration on a skin surface.

It is another object of the present invention to provide a pair of skin acupoint or meridian nitric oxide collection kits for assaying nitric oxide concentration on a skin surface of an acupoint or meridian and on a skin surface of a non-acupoint or non-meridian.

Accordingly, in order to accomplish the above objects, the present invention provides a skin acupoint or meridian nitric oxide collection kit, which comprises:

a nitric oxide collecting solution;

a collecting system, comprising:

a guiding body having a collecting cavity and a skin window, wherein said collecting cavity is adapted for receiving the nitric oxide solution when the nitric oxide collecting solution is placed into the collecting cavity of the guiding body and the skin window is adapted for acting as an opening to a skin surface so that said nitric oxide collecting solution is provided on a predetermined position of the skin surface;

an adhesive element for attaching and positioning the guiding body such that the guiding body is capable of providing on the predetermined position of a skin surface and the nitric oxide collecting solution is capable of retaining in the predetermined position of the skin surface; and means for collecting the nitric oxide collecting solution.

Furthermore, the present invention provides a skin acupoint/meridian nitric oxide collection method comprising the steps of:

a. providing a nitric oxide collecting solution A' having a predetermined concentration;

b. applying said nitric oxide collecting solution A' on a predetermined position of a skin surface for a predetermined period of time to form a final solution; and c. collecting said final solution.

BRIEF DESCRIPTION OF THE DRAWINGS

FIG. 8 is a method of collecting NO, nitrite and nitrate from a skin surface.

DETAILED DESCRIPTION OF THE PREFERRED EMBODIMENT

Figure 1:
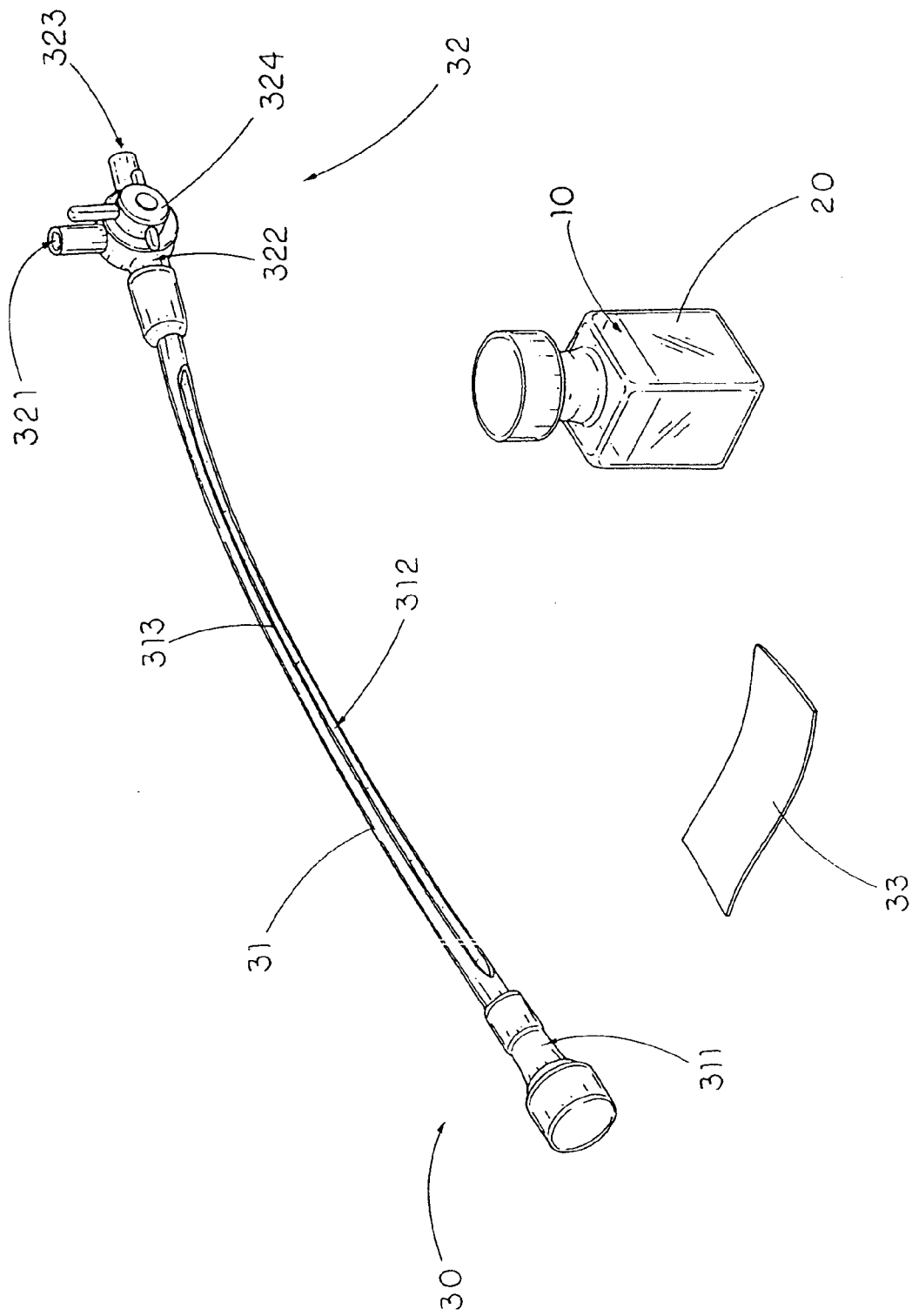
FIG. 1 is a perspective view of a skin acupoint or meridian nitric oxide collection kit according to a preferred embodiment of the present invention.

Referring to FIG. 1 of the drawings, a skin acupoint or meridian nitric oxide collection kit according to a preferred embodiment of the present invention is illustrated, wherein the collection kit of the present invention is adapted to collect nitric oxide (NO), nitrite and nitrate from a skin surface for determining nitric oxide concentrations in acupuncture points or meridians, so as to assay the nitric oxide of the skin.

As shown in FIG. 1, the collection kit comprises a nitric oxide (NO) collecting solution 10, a vial 20, and a collecting system 30. The collecting system 30 comprises a guiding body 31 having a first end 311, a collecting cavity 312 for receiving the NO collecting solution 10 therein, and a skin window 313 opened the collecting cavity 312 to the skin surface. The guiding body 31 further comprises a three-way switch 32 having a liquid inlet 321 adapted for injecting the NO collecting solution, a central vent 322 opened to the collecting cavity 312 of the guiding body 31, a liquid outlet 323 adapted for collecting a final NO collecting solution, and a control valve 324 for selectively communicating the central vent 322 between the liquid inlet 321 and the liquid outlet 323, and an adhesive element 33 for attaching and positioning the guiding body 31 such that the guiding body 31 is capable of providing and attaching on a predetermined position of the skin surface and the nitric oxide collecting solution 10 is capable of retaining in the predetermined position of the skin surface.

The guiding body 31 may further comprise a pressure controller provided at the first end of the guiding body, wherein the pressure controller is received in the guiding body and having a head protruded outwardly from the guiding body. By adjusting a length of the head of the pressure controller, a pressure inside the collecting cavity of the guiding body is capable of adjustment when the guiding body is attached on the skin.

According to the preferred embodiment, the NO collecting solution 10 is preferably a oxyhemoglobin solution of a predetermined concentration, or other solution such as oxymyoglobin to catalyze the conversion of NO or nitrite to nitrate, and the oxyhemoglobin solution is preferably approximately 10 μM in the above preferred embodiment. The NO collecting solution 10 is received in the collecting cavity 312 of the guiding body 31, which is exposed to the predetermined position of the skin surface through the skin window 313. Then after a predetermined period of time, which is approximately 20 minutes in the above preferred embodiment, the NO collecting solution 10 is collected. The NO collecting solution 10 is selected from a group of experiments to test different concentrations of hemoglobin and other solutions placed in the guiding body 31 on the skin surface for different periods of time in order to absorb nitric oxide, nitrite and nitrate on the skin surface.

The guiding body 31 is preferably a TYGON flexible plastic tube having a predetermined diameter and length. Accordingly, the guiding body 31 has a diameter from 0.2 to 0.5 centimeter and a length from 4 to 50 centimeters in the above preferred embodiment. It is known that acupuncture or meridian points are about 1 millimeter in diameter, therefore the collection kit features a TYGON flexible plastic tube that has a definite diameter and length.

The adhesive element 33 is preferably a sticker-type adhesive element such as 3M Tegaderm, a transparent dressing, or a liquid-type adhesive element such as a PeriAcryl Dental Formulation. The adhesive element 33 made of adhesive material for securing and positioning the guiding body 31 such that the guiding body 31 is capable of providing on a predetermined position of a skin surface and the nitric oxide collecting solution 10 is capable of retaining in the predetermined position of the skin surface. The adhesive element 33 prevents any leakage of the NO collecting solution 10 from the guiding body 31. The 3M Tegaderm and the PeriAcryl Dental Formulation are researched to be the most efficient adhesive materials for the collection kit of the present invention because they are very effective, non-toxic, and does not harm human's skin or animal's skin. Of course, any kinds of adhesive materials may be used as the adhesive element 33 provided that the adhesive materials are effective, non-toxic and harmless to the skin surface.

Therefore, by switching the control valve 324 for the liquid inlet 321 communicating with the central vent 322, the NO collecting solution 10 is injected into the collecting cavity 312 of the guiding body 31. The nitric oxide concentration of the skin surface is absorbed by the nitric oxide collecting solution 10 to form a final solution inside the collecting cavity 312 of the guiding body 31, and then by switching the control valve 324 for the central vent 322 communicating with the liquid outlet 323, the final solution is collected to the collecting vial 20 through the liquid outlet 323.

The collecting kit of the present invention should be conducted following the operation manual. Human use is recommended to be performed or directed by certified or licensed physicians and complementary and alternative medicine (CAM) practitioners with experience in the areas such as acupuncture, acupressure, chiropractic medicine, therapeutic touch, Reiki, Tuna, laying-on-of-hands, Qi Gong and other CAM. Locations of acupoints or meridians will be detected by corresponding to the acupoints of animals and human described in the "Chinese classical topography and or measurements of low electrical resistance characteristics". The collecting system 30 will be fixed to the skin surface containing acupuncture points or meridians. The NO collecting solution 10 will be placed inside the guiding body 31 and exposed to the skin surface for a predetermined period of time, which is about 20 minutes in the above preferred embodiment. Each time, the final solution will be collected via the three-way switch 32 for assaying NO, nitrite and nitrate concentration.

For the usage of the present invention, Meridian theory is an essential pathway system and the core theory of acupuncture, acupressure, chiropractic medicine, therapeutic touch, Reiki, Tuna, laying-on-off-hands, Qi Gong and other complementary and alternative medicines. These findings will establish a firm scientific basis for the therapies and make it possible to identify acupoints or meridians for research, education, diagnosis and treatment. Collections of NO, nitrite and nitrate from the skin surface using the kit will be possible to assay NO concentrations from the acupoints or meridians for research, diagnosis and treatment using alternative therapies.

Figure 2:
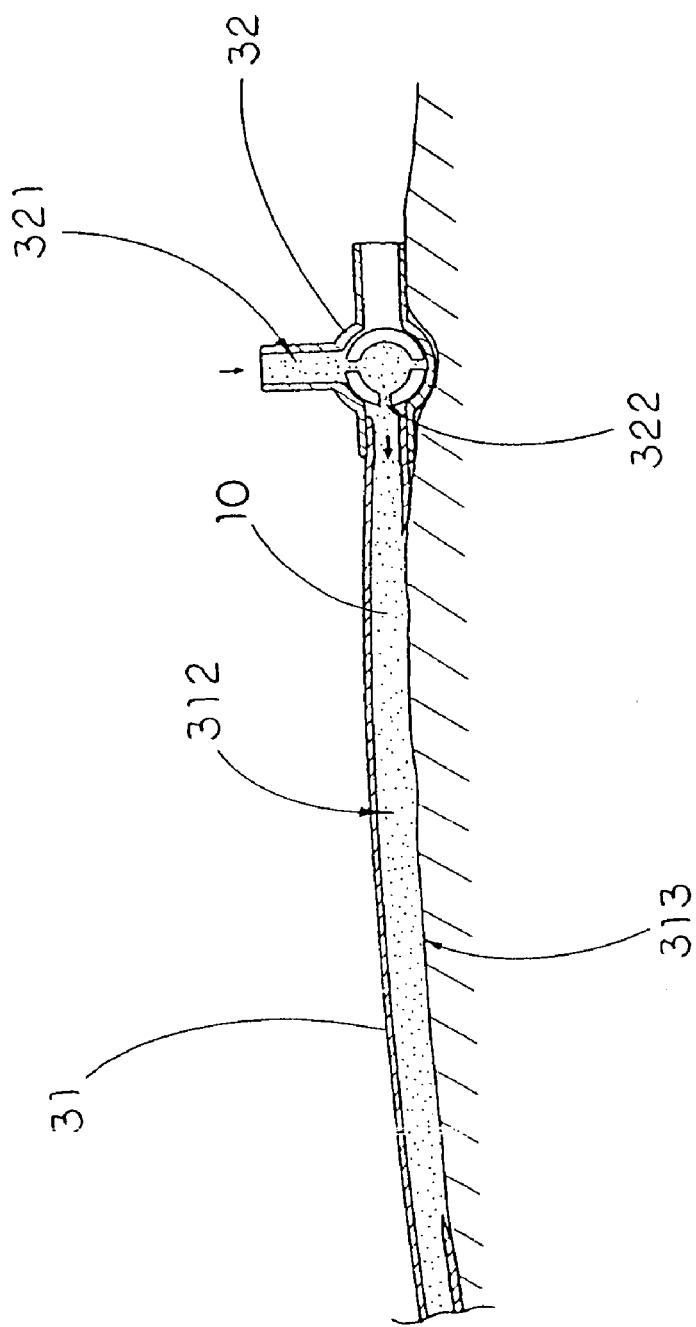
FIG. 2 is a partially sectional view of the skin acupoint or meridian nitric oxide collection kit applied on a skin surface according to the above preferred embodiment of the present invention, wherein a central vent is communicating with a liquid inlet.

Referring to FIG. 2 of the drawings, the collecting system 30 of the skin acupoint or meridian nitric oxide collection kit of the above preferred embodiment is illustrated and the three-way switch 32 is in an injecting position. The skin window 313 is opened to the skin surface so that the NO collecting solution inside the collecting cavity 312 of the guiding body 31 is exposed to the skin surface for collecting NO, nitrite and nitrate. When the three-way switch 32 is in the injecting position, the central vent 322 is communicating with the liquid inlet 321 and the NO solution is capable of injecting to the collecting cavity 312 of the guiding body 31 through the central vent 322 and the liquid inlet 321.

Figure 3:
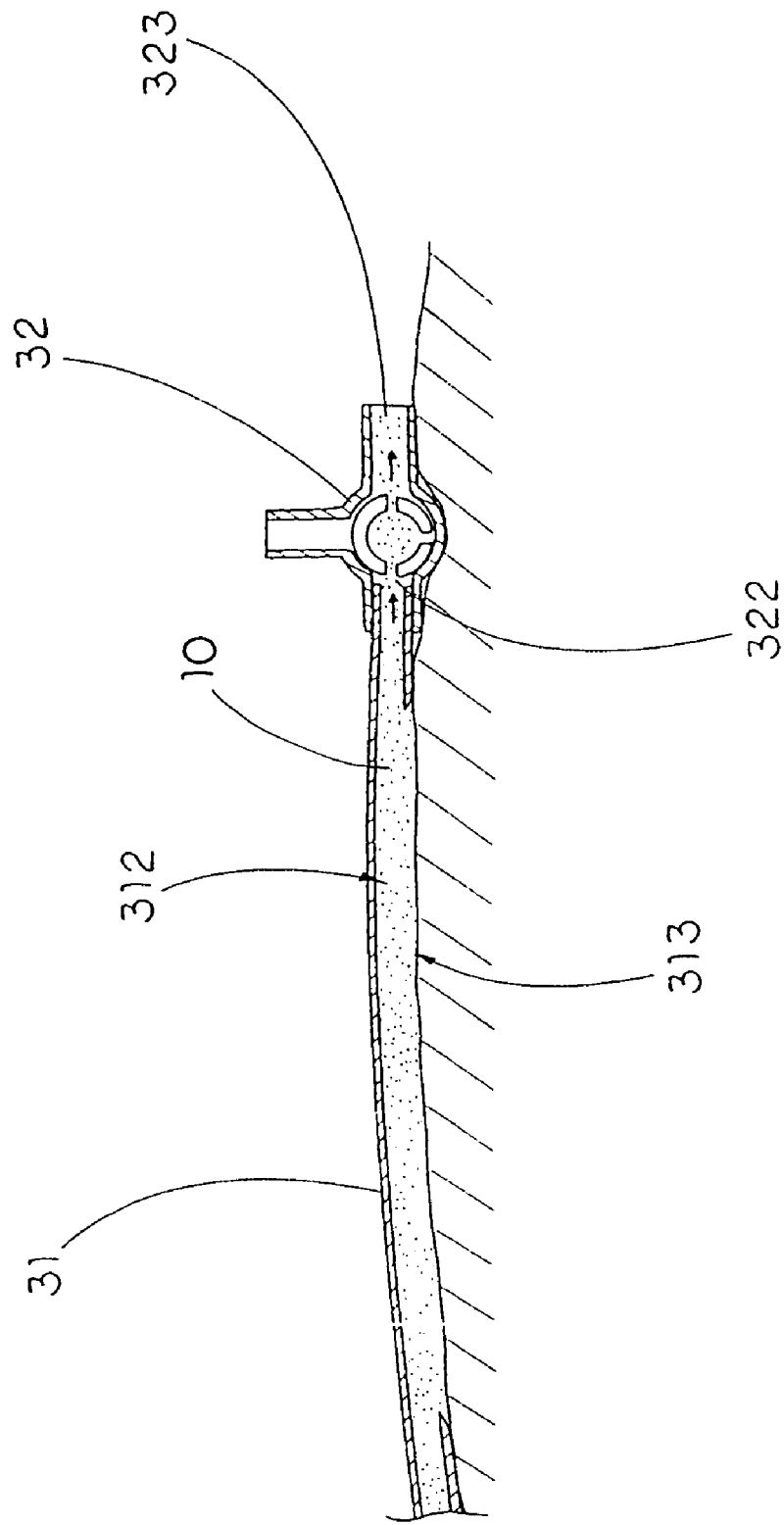
FIG. 3 is a partially sectional view of the skin acupoint or meridian nitric oxide collection kit applied on a skin according to the above preferred embodiment of the present invention, wherein a central vent is communicating with a liquid outlet.

Referring to FIG. 3 of the drawings, a collecting system 30 of a skin acupoint or meridian nitric oxide collection kit of the above preferred embodiment is illustrated. The three-way switch 32 is in a collecting position, wherein the central vent 322 is communicating with the liquid outlet 323 and the NO solution is collected to the vial 20 through the central vent 322 and the liquid outlet 323.

Figure 4:
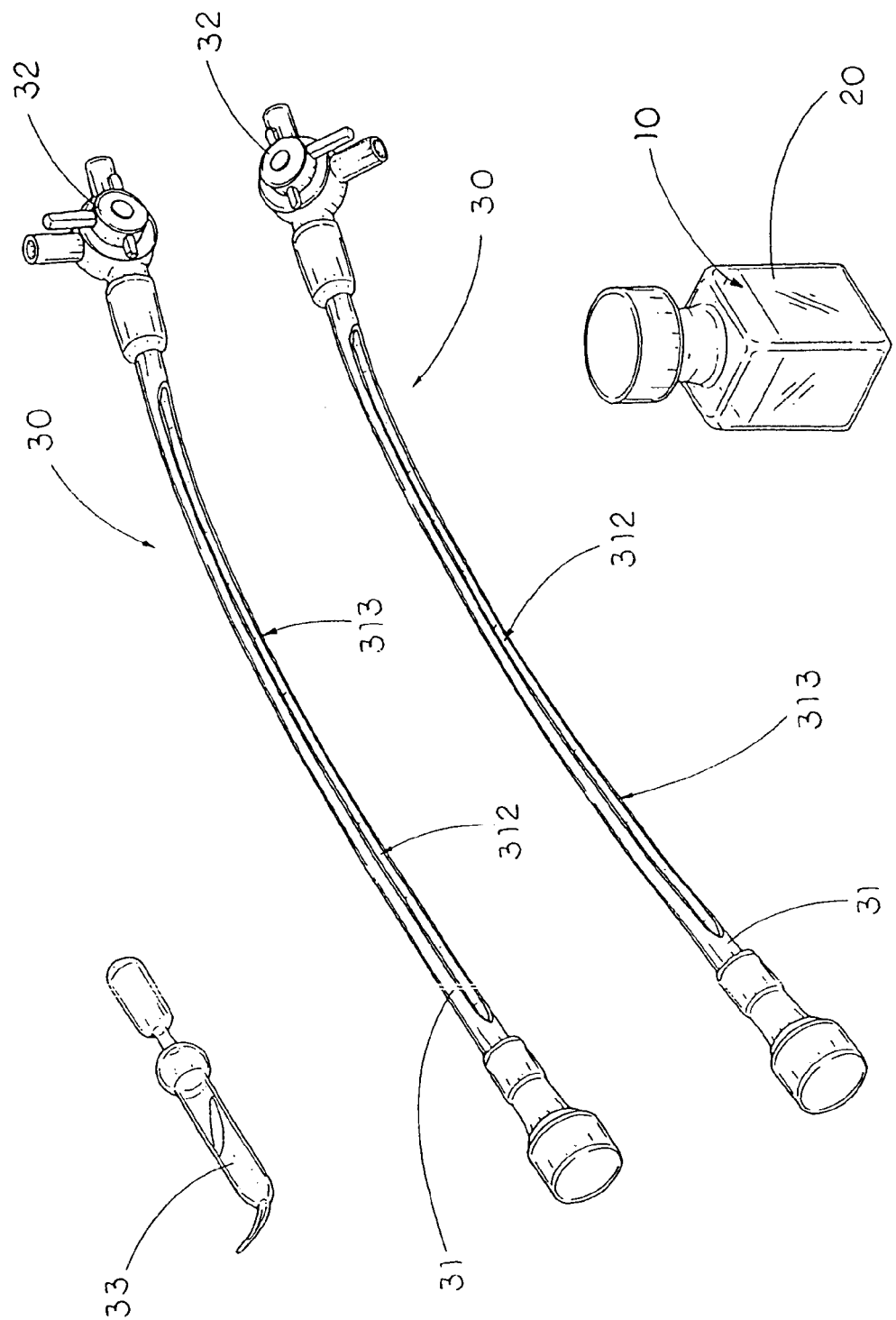
FIG. 4 is a perspective view of the skin acupoint or meridian nitric oxide collection kit according to the above preferred embodiment of the present invention, wherein PeriAcryl Dental Formulation is used as an adhesive element.

Referring to FIG. 4 of the drawings, the skin acupoint or meridian nitric oxide colleciton kit according to the above preferred embodiment of the present invention is illustrated, wherein a PeriAcryl Dental Formulation is used as the adhesive element 33. The PeriAcryl Dental Formulation is applied to the skin window 313 of the collecting system 30 so that the guiding body 31 is secured and positioned in the predetermined position of a skin surface and leakage of NO collecting solution 10 is prevented.

Figure 5:
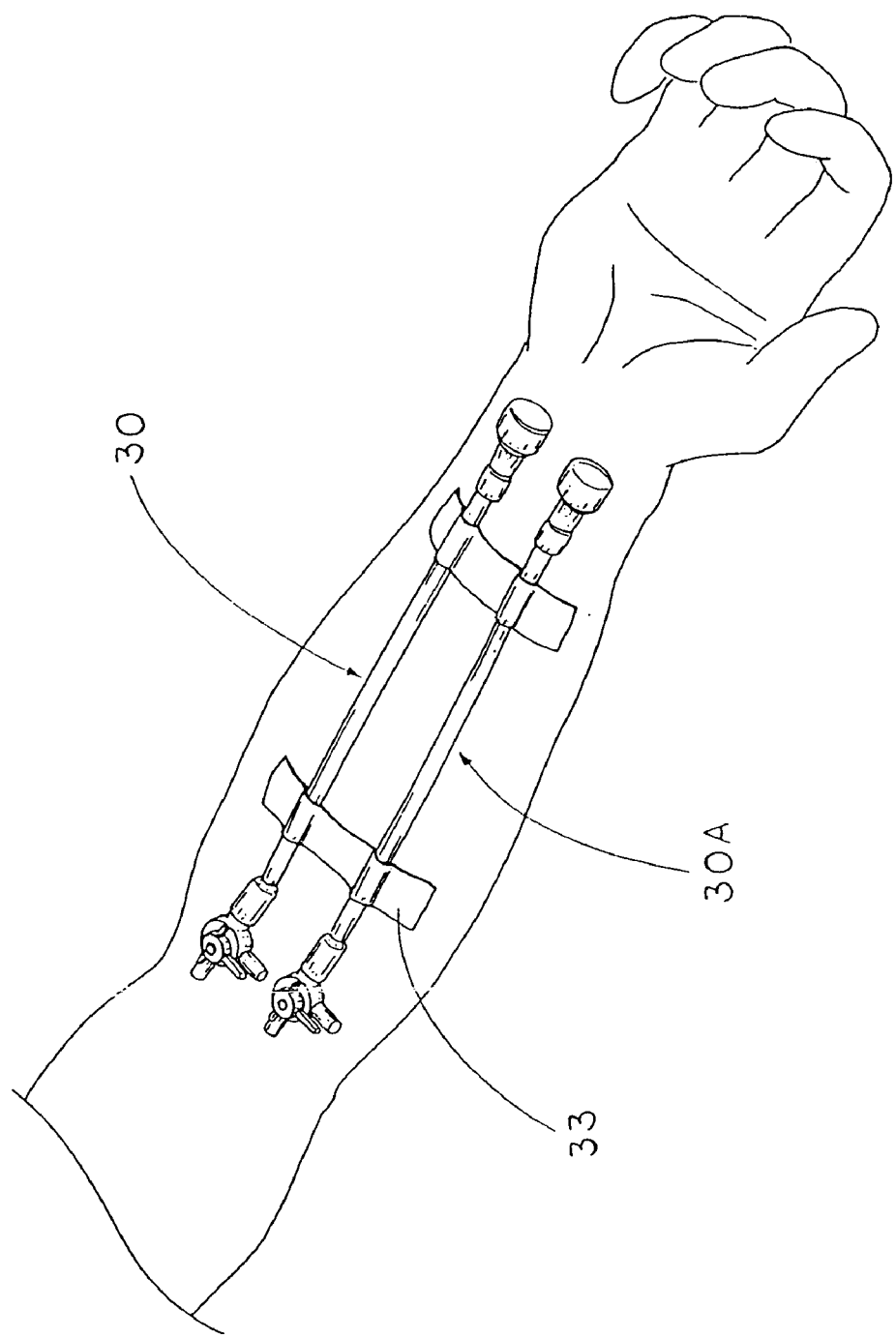
FIG. 5 is a perspective view of the skin acupoint or meridian nitric oxide collection kit applied on the skin according to the above preferred embodiment of the present invention, wherein two collecting systems are shown and two 3M Tegaderm are used as adhesive element.

Referring to FIG. 5, the skin acupoint or meridian nitric oxide collection kit is applied on the skin surface according to the above preferred embodiment of the present invention, and a 3M Tegaderm is used as adhesive element 33. The collecting system 30 is applied to the skin surface of an acupoint or meridian and a second collecting system 30A is applied to the skin surface of a non-acupoint or non-meridian. The collecting system 30 is used to assay NO concentration of acupoint or meridian while the second collecting system 30A is acted as a control for assaying NO concentration of non-acupoint or meridian. Therefore, comparison of the NO concentrations of the skin surface having an acupoint or meridian and a non-acupoint or non-meridian can be made.

Figure 6:
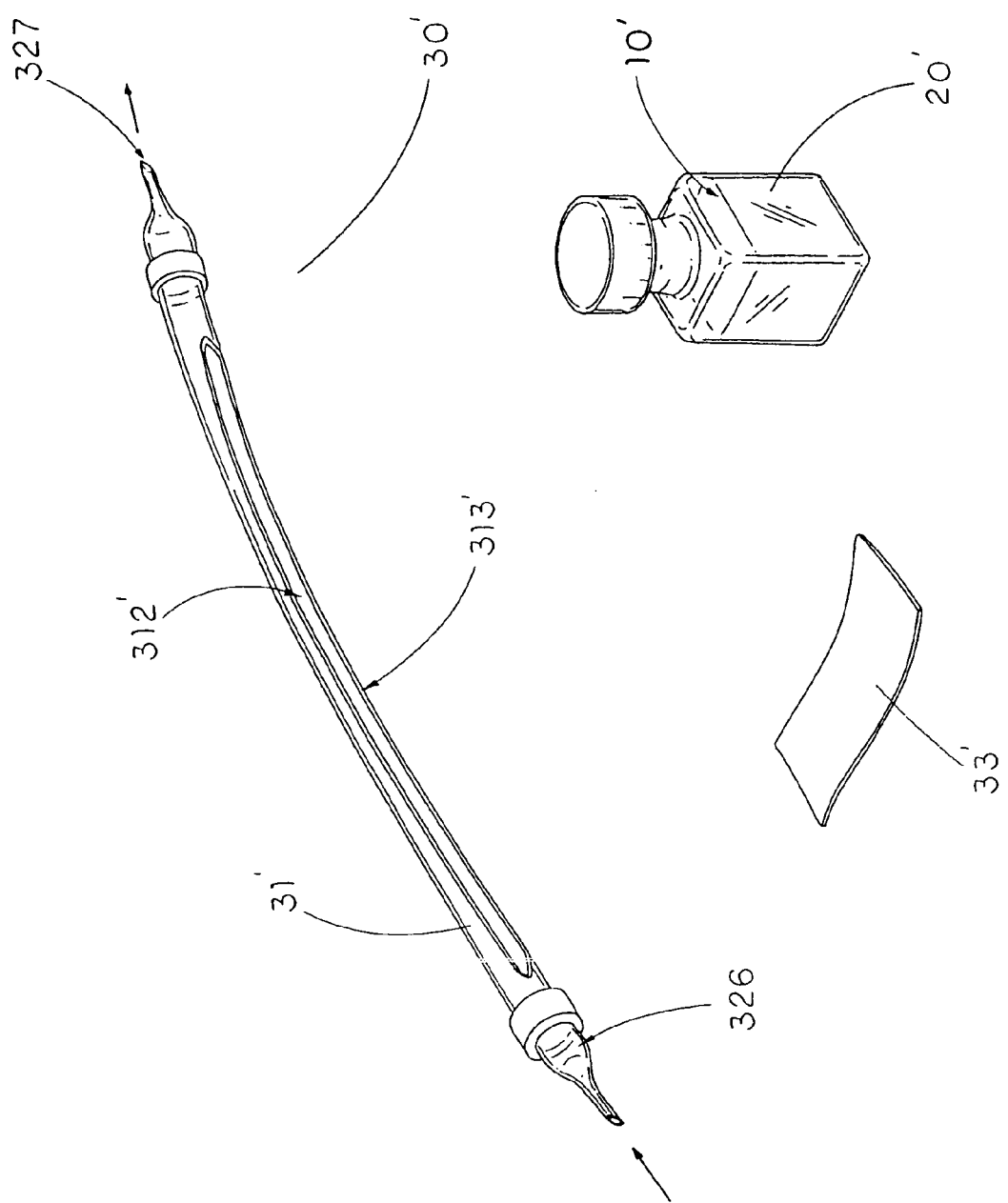
FIG. 6 is a perspective view of a collecting system of a skin acupoint or meridian nitric oxide collection kit according to a second preferred embodiment of the present invention.

Referring to FIG. 6 of the drawings, the collection kit comprises a nitric oxide (NO) collecting solution 10', a vial 20', and a collecting system 30'. The collecting system 30' comprises a guiding body 31' having a collecting cavity 312' for receiving the NO collecting solution 10' therein, a injecting vent 326 adapted for injecting the NO solution, and a collecting vent 327 adapted for collecting the NO solution 10', and an adhesive element 33' for attaching and positioning the guiding body 31' such that the guiding body 31' is capable of providing on a predetermined position of a skin surface and the nitric oxide collecting solution 10' is capable of retaining in the predetermined position of the skin surface through the skin window 313'.

Therefore, the NO collecting solution 10' is injected into the collecting cavity 312' through the injecting vent 326. The nitric oxide concentration of a skin surface is absorbed by the nitric oxide collecting solution 10' to form a second final solution inside the collecting cavity 312' of the guiding body 31', and then the second final solution is collected to the collecting vial 20' through the collecting vent 327.

Figure 7:
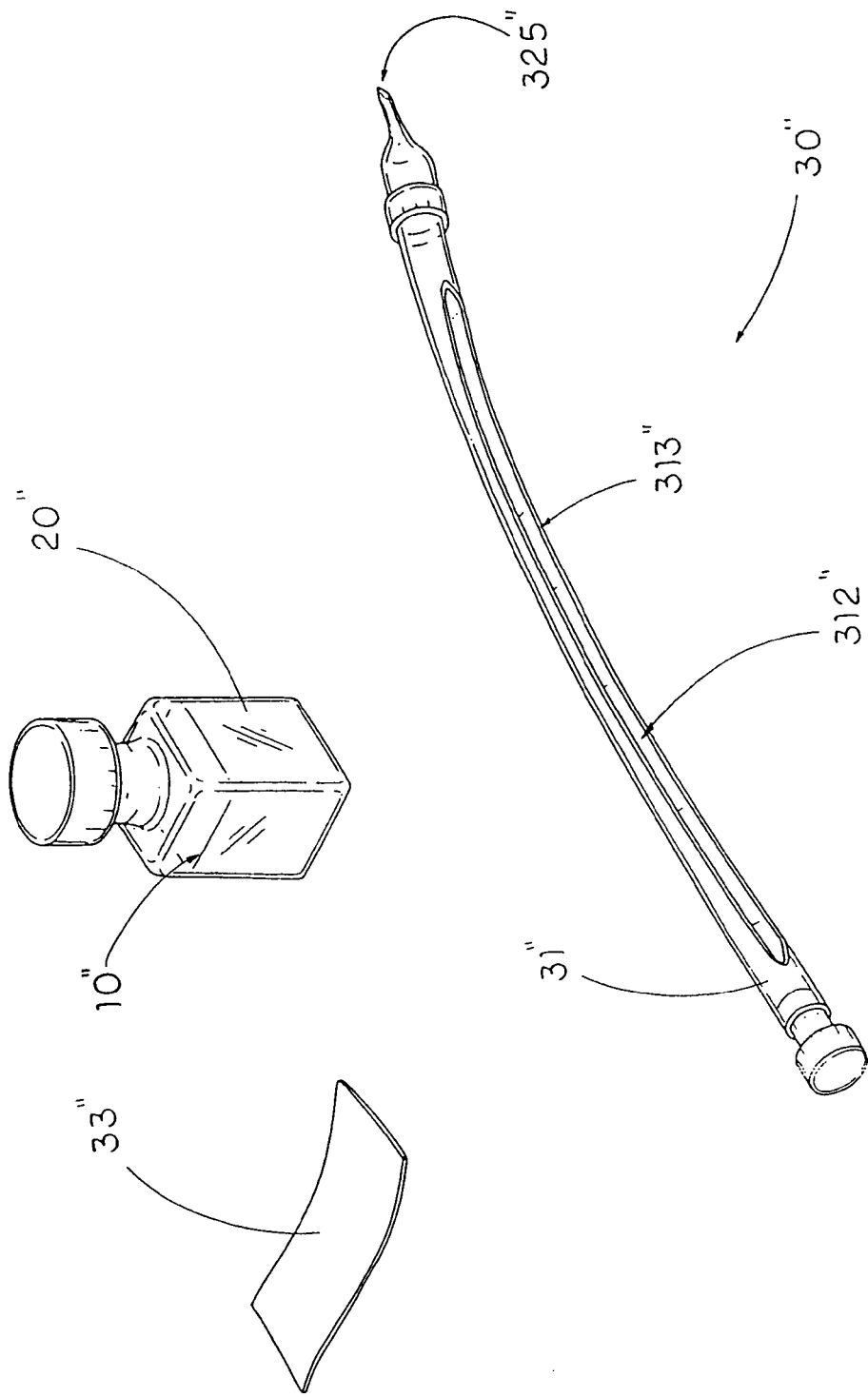
FIG. 7 is a perspective view of a collecting system of a skin acupoint or meridian nitric oxide collection kit according to a third preferred embodiment of the present invention.

Referring to FIG. 7 of the drawings, the collection kit comprises a nitric oxide (NO) collecting solution 10", a vial 20", and a collecting system 30". The collecting system 30" comprises a guiding body 31" having a collecting cavity 312" for receiving the NO collecting solution 10" therein, a liquid vent 325" adapted for injecting the NO solution when injecting NO solution 10" into the guiding body 31', and adapted for collecting the NO solution 10" when collecting the NO solution into the vial 20". The collection kit further comprises an adhesive element 33" for attaching and positioning the guiding body 31" such that the guiding body 31" is capable of providing on a predetermined position of a skin surface and the nitric oxide collecting solution 10" is capable of retaining in the predetermined position of the skin surface.

Therefore, NO collecting solution 10" is injected into the collecting cavity 312" through the liquid vent 325. The nitric oxide concentration of the skin surface is absorbed by the nitric oxide collecting solution 10" to form a final solution inside the collecting cavity 312" of the guiding body 31", and then the final solution is collected to the collecting vial 20" through the liquid vent 325.

Referring to FIG. 8 of the drawings, NO, nitrite, and nitrate are collected by a method comprising the steps of:

a. providing a NO collecting solution having a predetermined concentration on a predetermined position of a skin surface for a predetermined period of time to form a final solution; and b. collecting the final solution for analysis.

The NO collecting solution is preferably a oxyhemoglobin solution of a predetermined concentration, or other solution such as oxymyoglobin to catalyze the conversion of NO or nitrite to nitrate, and the oxyhemoglobin solution is preferably approximately 10 µM.

The final solution is preferably collected and stored in a plastic made collecting vial and analyzed using chemiluminescence NO Analyzer, electrochemical electrode system or other methods.

Under room temperature, the time is preferably at least about 10 minutes. Normally, the time is in a range of 10 to 40 minutes and the preferred time is 20 minutes.

Figure 9:
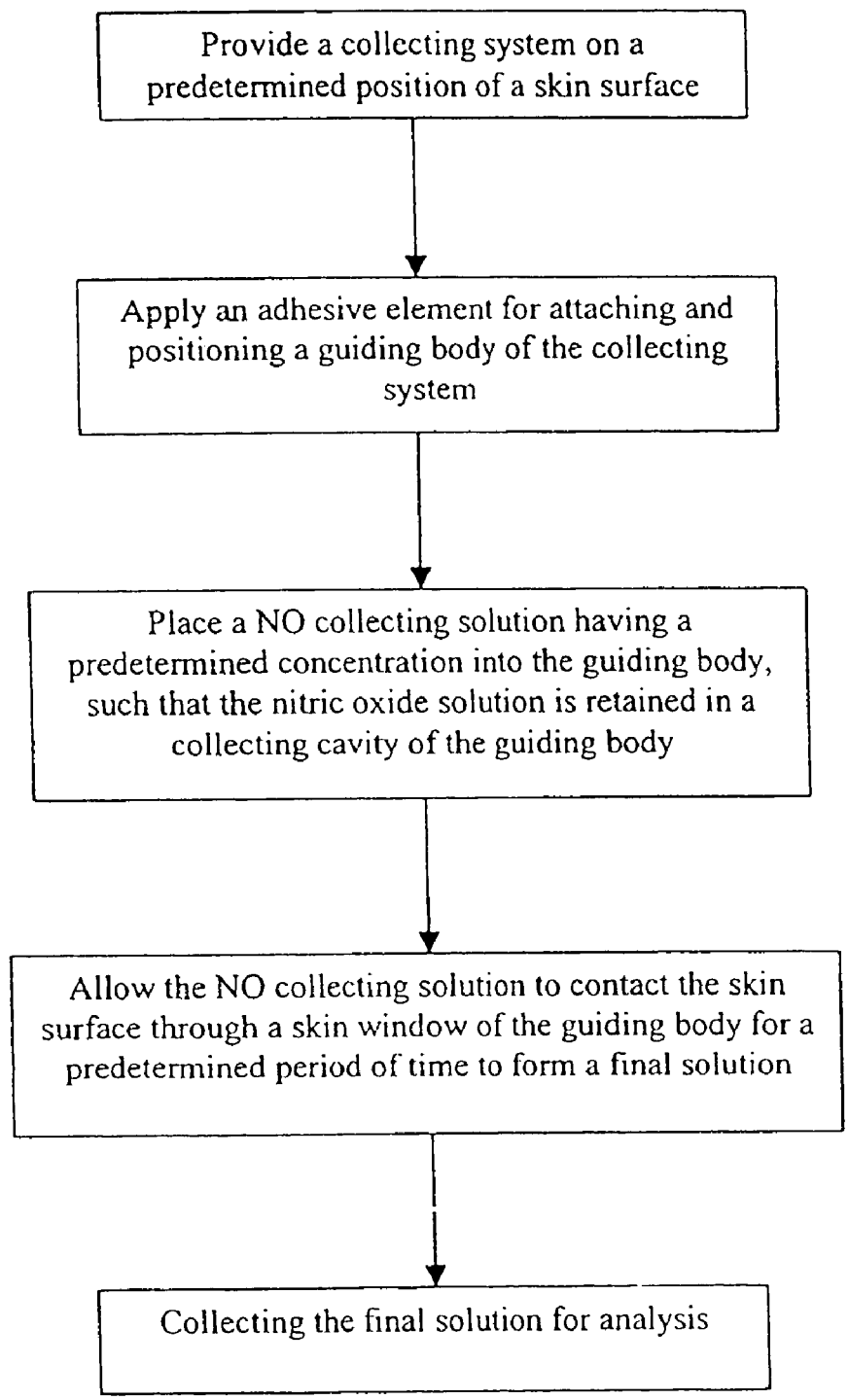
FIG. 9 is a method of collecting NO, nitrite and nitrate from a skin surface by using a skin acupoint or meridian nitric oxide collection kit.

Referring to FIG. 9 of the drawings, NO, nitrite, and nitrate is collected from a method by using a skin acupoint or meridian nitric oxide collection kit comprising the steps of:

a. providing a collecting system on a predetermined position of a skin surface;

b. applying an adhesive element for attaching and positioning a guiding body of the collecting system such that the guiding body is capable of providing on a predetermined position of a skin surface;

c. placing a NO collecting solution having a predetermined concentration into the guiding body, such that the nitric oxide solution is retained in a collecting cavity of the guiding body;

d. allowing the NO collecting solution to contact the skin surface through a skin window of the guiding body for a predetermined period of time to form a final solution; and e. collecting the final solution for analysis.

The NO collecting solution is preferably a oxyhemoglobin solution of a predetermined concentration, or other solution such as oxymyoglobin to catalyze the conversion of NO or nitrite to nitrate, and the oxyhemoglobin solution is preferably approximately 10 μM.

The final solution is preferably collected and stored in a plastic made collecting vial and analyzed using chemiluminescence NO analyzer, electrochemical electrode system or other methods.

Under room temperature, the time is preferably at least about 10 minutes. Normally, the time is in a range of 10 to 40 minutes and the preferred time is 20 minutes.

The adhesive element 33 is preferably a sticker-type adhesive element such as 3M Tegaderm, a transparent dressing, or a liquid-type adhesive element such as a PeriAcryl Dental Formulation. The adhesive element 33 is made of adhesive material for securing and positioning the guiding body. The adhesive element prevents any leakage of the NO collecting solution from the guiding body. The 3M Tegaderm and the PeriAcryl Dental Formulation are researched to be the most efficient adhesive materials for the collection kit of the present invention because they are very effective, non-toxic, and does not harm human's skin or animal's skin. Of course, any kinds of adhesive materials may be used as the adhesive element 33 provided that the adhesive materials are effective, non-toxic and harmless to the skin surface.

What is claimed is:

1. A skin acupoint/meridian nitric oxide collection method by using a skin acupoint/meridian nitric oxide collection kit, comprising the steps of:
    (a) locating a tubular guiding body of said collection kit on a skin surface, wherein said guiding body having a collecting cavity and a skin window provided on a wall surface of said guiding body to communicate with said collecting cavity;
    (b) retaining said guiding body on said skin surface at position that said skin window acts as an opening of said collecting cavity of said guiding body to communicate said collecting cavity with said skin surface through said skin window
    (c) injecting a nitric oxide collecting solution having a predetermined concentration into said collecting cavity, wherein said nitric oxide collecting solution within said collecting cavity is adapted for applying to said skin surface through said skin window;
    (d) allowing said nitric oxide collecting solution to absorb nitrate and nitrite from said skin surface for a predetermined period of time so as to collect said nitrate and nitrite from said skin surface without penetrating said guiding body through said skin surface to form a final solution; and
    (e) collecting said final solution from said collecting cavity for assaying nitric oxide concentration of said skin surface.

2. The method, as recited in claim 1, wherein said nitric oxide collecting solution is a solution containing NO scavenging compound.

3. The method as recited in claim 2, wherein said solution containing NO scavenging compound includes an oxyhemoglobin solution.

4. The method as recited in claim 1, in step (b), wherein a peripheral area of said skin window of said guiding body is adhered on said skin surface to ensure said nitric oxide collecting solution applying on said skin surface.

5. The method as recited in claim 2, in step (b), wherein a peripheral area of said skin window of said guiding body is adhered on said skin surface to ensure said nitric oxide collecting solution applying on said skin surface.

6. The method as recited in claim 1, in step (a), wherein said guiding body is located at an acupoint-meridian area of said skin surface to collect said final solution.

7. The method as recited in claim 2, in step (a), wherein said guiding body is located at a predetermined part of derma including an acupoint-meridian area of said skin surface to collect said final solution.

8. The method as recited in claim 5, in step (a), wherein said guiding body is located at a predetermined part of derma including an acupoint-meridian area of said skin surface to collect said final solution.

9. The method, as recited in claim 6, further comprising the steps of:
    (a') providing a supplemental collecting kit, which is identical to said collecting kit, on said skin surface to collect a second final solution at a non-acupoint-meridian area of said skin surface; and
    (b') comparing said two final solutions respectively collected from said acupoint-meridian area and said non-acupoint-meridian area of said skin surface.

10. The method, as recited in claim 7, further comprising the steps of:
    (a') providing a supplemental collecting kit, which is identical to said collecting kit, on said skin surface to collect a second final solution at a non-acupoint-meridian area of said skin surface; and
    (b') comparing said two final solutions respectively collected from said acupoint-meridian area and said non-acupoint-meridian area of said skin surface.

11. The method, as recited in claim 8, further comprising the steps of:
    (a') providing a supplemental collecting kit, which is identical to said collecting kit, on said skin surface to collect a second final solution at a non-acupoint-meridian area of said skin surface; and
    (b') comparing said two final solutions respectively collected from said acupoint-meridian area and said non-acupoint-meridian area of said skin surface.

* * * * *